United States Patent
Pellegrini

(10) Patent No.: US 12,394,051 B2
(45) Date of Patent: Aug. 19, 2025

(54) METHOD AND SYSTEM OF DETECTING CLIPPING OF AN OCT IMAGE

(71) Applicant: OPTOS PLC, Dunfermline (GB)

(72) Inventor: Enrico Pellegrini, Dunfermline (GB)

(73) Assignee: OPTOS PLC, Dunfermline (GB)

( * ) Notice: Subject to any disclaimer, the term of this patent is extended or adjusted under 35 U.S.C. 154(b) by 435 days.

(21) Appl. No.: 18/084,157

(22) Filed: Dec. 19, 2022

(65) Prior Publication Data

US 2023/0316508 A1 Oct. 5, 2023

(30) Foreign Application Priority Data

Apr. 4, 2022 (EP) .................................... 22166464

(51) Int. Cl.
| | | |
|---|---|---|
| *G06K 9/00* | (2022.01) | |
| *A61B 6/03* | (2006.01) | |
| *G06T 7/00* | (2017.01) | |
| *G06T 7/13* | (2017.01) | |
| *G06T 7/70* | (2017.01) | |

(52) U.S. Cl.
CPC .............. *G06T 7/0012* (2013.01); *G06T 7/13* (2017.01); *G06T 7/70* (2017.01); *G06T 2207/10101* (2013.01); *G06T 2207/30041* (2013.01)

(58) Field of Classification Search
CPC ................ G06K 9/00; G06T 7/00; A61B 6/03
USPC ........ 382/100, 103, 106, 117, 118, 128–133, 382/154, 155, 162, 168, 173, 181, 199, 382/219, 224, 254, 276, 286–291, 305, 382/312, 321; 378/4, 21, 42
See application file for complete search history.

(56) References Cited

U.S. PATENT DOCUMENTS

| | | | |
|---|---|---|---|
| 2010/0220914 A1* | 9/2010 | Iwase ................... | G06T 7/0012 |
| | | | 382/131 |
| 2012/0140179 A1 | 6/2012 | Miyasa et al. | |
| 2017/0021572 A1 | 1/2017 | Wiesner et al. | |
| 2017/0215725 A1 | 8/2017 | Ishiai | |
| 2018/0051977 A1* | 2/2018 | Bagherinia ............ | A61B 3/102 |
| 2020/0320693 A1* | 10/2020 | Robertson .............. | A61B 5/021 |

(Continued)

FOREIGN PATENT DOCUMENTS

JP    WO 2011/018950 A1    2/2011

OTHER PUBLICATIONS

OCT (Year: 2022).*

(Continued)

*Primary Examiner* — Seyed H Azarian
(74) *Attorney, Agent, or Firm* — FAEGRE DRINKER BIDDLE & REATH

(57) ABSTRACT

Aspects of the present invention relate to a method of detecting clipping of retinal image content in an optical coherence tomography, OCT, image of a patient's retina. The method comprises detecting a boundary of the retinal image content in the OCT image and calculating a distance between the boundary and an edge of the OCT image. The method further comprises determining if clipping of the retinal image content in the OCT image has occurred by comparing the calculated distance between the boundary and the edge of the OCT image with a clipping threshold distance. Clipping of the retinal image content is determined to have occurred when the calculated distance between the boundary and the edge of the OCT image is equal to, or less than, the clipping threshold distance.

14 Claims, 7 Drawing Sheets

(56) References Cited

U.S. PATENT DOCUMENTS

2021/0038071 A1* 2/2021 Tatara .................... A61B 3/102
2024/0394874 A1* 11/2024 Brandt .................. G06T 7/0002

OTHER PUBLICATIONS

OCT (Year: 2025).*
Extended European Search Report (EESR) dated Sep. 29, 2022 issued on the priority European patent application 22 166 464.2 (7 sheets).

* cited by examiner

METHOD AND SYSTEM OF DETECTING CLIPPING OF AN OCT IMAGE

This application claims the benefit of priority of European Patent Application No. EP 22 166 464.2 filed Apr. 4, 2022, the content of which is incorporated by reference herein in its entirety, as if set forth fully herein.

FIELD

Example aspects herein generally relate to detecting clipping of an optical coherence tomography image, in particular, but not exclusively, to a method and system for detecting vertical clipping of retinal imaging content in an optical coherence tomography, OCT, image such as in an OCT B-scan.

BACKGROUND

Optical coherence tomography (OCT) is a non-invasive imaging method used to generate cross-sectional images of tissue. OCT imaging is commonly used in ophthalmology to generate cross-sectional images of a patient's retina. The resultant cross-sectional images of the retina can allow a clinician to gain an understanding of the retinal tissue of a patient's eye such that pathogens can be identified in the retinal tissue.

In OCT imaging, several one-dimensional A-scans are performed at different imaging depths within the tissue such that the A-scans can be combined to create a two-dimensional B-scan. The depth at which the A-scans are acquired is varied such that a cross-sectional image of the tissue may be generated in the B-scan.

During OCT imaging the B-scans that are acquired by the OCT imaging system can be clipped resulting in regions of the tissue to be imaged being cropped from the B-scan. Vertical clipping is a common problem during OCT image acquisition as a result of misalignment of a patient relative to the OCT scanning system. In retinal imaging, vertical clipping occurs in a B-scan where the top and/or bottom boundaries of a B-scan crop the retinal content to be imaged such that the entire depth of the retina to be imaged is not captured within the boundaries of the B-scan.

Clipping may be caused by a patient being located incorrectly relative to the OCT imaging system during image acquisition or, for example, the OCT imaging system being incorrectly configured to acquire OCT images of the tissue. During retinal imaging in which the B-scan is an image of the patient's retina, clipping of the retinal image content may occur as a result of the patient's head being located incorrectly relative to the OCT imaging system during image acquisition.

Currently OCT imaging systems do not provide an indication of a level of clipping of the resultant OCT images acquired by the imaging system to a clinician. This can result in the patient leaving the clinic by the time the clinician reviews the OCT images of the patient at which point the clinician would identify that clipping had occurred. In some instances where clipping of the patient's tissue in the OCT images is severe the clinician may have to recall the patient to the clinic to repeat the OCT imaging procedure. There is therefore a need to provide the clinician with an indication that an OCT imaging procedure has accurately captured OCT images of the tissue to be imaged following OCT image acquisition.

SUMMARY

According to an example aspect herein, a method of detecting clipping of tissue image data in an optical coherence tomography, OCT, image of tissue is provided, the method comprising: detecting a boundary of the tissue image data in the OCT image; calculating a distance between the boundary and an edge of the OCT image; and determining if clipping of the tissue image data in the OCT image has occurred by comparing the calculated distance between the boundary and the edge of the OCT image with a clipping threshold distance; wherein clipping of the tissue image data is determined to have occurred when the calculated distance between the boundary and the edge of the OCT image is equal to, or less than, the clipping threshold distance.

According to a further example aspect herein, there is provided a method of detecting clipping of retinal image content or retinal image data in an optical coherence tomography, OCT, image of a patient's retina, the method comprising: detecting a boundary of the retinal image data in the OCT image; calculating a distance between the boundary and an edge of the OCT image; and determining if clipping of the retinal image data in the OCT image has occurred by comparing the calculated distance between the boundary and the edge of the OCT image with a clipping threshold distance; wherein clipping of the retinal image data is determined to have occurred when the calculated distance between the boundary and the edge of the OCT image is equal to, or less than, the clipping threshold distance.

The method can detect clipping, and in particular vertical clipping, of retinal content within an OCT image of a patient's retina. Vertical clipping of retinal content or retinal image data in an OCT image can result in regions of a patient's retina being cropped from an OCT image such that areas of the patient's retina are missed from the OCT image. This may result in the patient having to return for a further OCT scan of their retina to acquire complete OCT images of the retina. The method can be performed in substantially real-time when acquiring OCT images of a patient's retina and an output may be provided to a clinician to notify them of the presence of vertical clipping of the retinal content. The output can be provided to the clinician shortly after imaging of the retina is completed, prior to the patient leaving the clinic. The clinician may then re-position the patient and repeat the OCT scan to acquire OCT images that contain the retinal content of the patient.

In one embodiment the method may comprise: detecting a second boundary of the retinal image data in the OCT image; calculating a distance between the second boundary and a second edge of the OCT image; and determining if clipping of the retinal image data has occurred by comparing the distance between the second boundary and the second edge of the OCT image with the clipping threshold distance; wherein clipping of the retinal image data is determined to have occurred when the distance between the second boundary and the second edge of the OCT image is equal to, or less than, the clipping threshold distance.

Detecting the position of two boundaries and comparing the distance between each boundary and a respective edge of the OCT image can allow vertical clipping at an upper and lower region of the retinal image data to be detected. In an example embodiment herein, the two boundaries may be lateral boundaries of an anatomical feature and horizontal clipping at lateral regions of the retinal image data to be detected.

In an embodiment the boundary may be an upper boundary of the retinal image data. The second boundary may be a lower boundary of the retinal image data. For example, the upper boundary may be an upper surface of the patient's retina and the lower boundary may be a lower surface of the patient's retina. The retinal image data may extend laterally across the width of the OCT image. The retinal image data may extend along a generally arcuate path such that the distance between the boundaries of the retinal image data and a respective edge of the OCT image varies along a length of the boundary.

Calculating the distance between the boundary and the edge of the OCT image may comprise calculating a distance between the upper boundary and an upper edge of the OCT image. Furthermore, calculating the distance between the second boundary and the second edge of the OCT image may comprise calculating a distance between the lower boundary and a lower edge of the OCT image.

In an embodiment the method may comprise outputting a clipping notification indicative of a level of clipping of the retinal image data in the OCT image. Clipping of the upper boundary and clipping of the lower boundary may be determined independently. A clipping notification may be output to convey a level of clipping of the upper boundary and or a level of clipping of the lower boundary. The clipping notification may be a clipping region overlaid on an image of the patient's retina. The clipping region may provide a visual indication to a clinician of areas of the retinal image data that have been clipped. The clipping region may vary in colour in dependence on a severity of clipping at a given location.

Determining if clipping of the retinal image data has occurred may further comprise comparing a location of the retinal image data with a clipping masked region. The clipping masked region may be a region encompassing a region of interest to be imaged by the OCT imaging system.

Determining if clipping of the retinal image data has occurred at the location may comprise: determining that the calculated distance between the boundary and the edge of the OCT image is equal to, or less than, the clipping threshold distance at the location; and determining that the location of the retinal image data is within the clipping masked region.

In an example embodiment herein, the clipping masked region can allow clipped regions of retinal image data to be discarded if they are outside the clipping masked region. This can allow the method to be used to detect clipping of the retinal image data that adversely affects the quality of the resultant OCT image of the area that a clinician is imaging. For example, if a clinician is imaging an anatomical feature on a patient's retina the masked region may encompass the anatomical feature. The clipping notification output to the clinician may provide an indication of a level of clipping of the masked region in the OCT image. The method may comprise positioning the clipping masked region at a position that encompasses an anatomical feature or region of interest on the patient's retina.

In one embodiment the method may comprise receiving positional data indicative of a position of the patient's eye. Furthermore, the method may comprise moving the boundary of the retinal image data in dependence on the received positional data. The method can compensate for movements of the patient's eye prior to determining the position of the boundary of the retinal image data. The positional data indicative of the patient's eye may be acquired by retinal tracking or the like.

The method may comprise acquiring the OCT image wherein the OCT image is one or more B-scans. Each B-scan may comprise a plurality of A-scans. The method may further comprise receiving boundary data indicative of a position of the boundary in the OCT image. The boundary data may be in the form of an array.

In a further embodiment the clipping threshold distance may be equal to zero. When the clipping threshold distance is equal to zero clipping of the retinal image data is deemed to have occurred when the boundary of the retinal image data intersects an edge of the OCT image. In another embodiment the clipping threshold distance may be defined as a function of the height of the OCT image or as an absolute distance. The clipping threshold distance may be defined at a distance from the edge of the OCT image where the quality of the OCT image is sufficiently high to obtain a clear image of the patient's retina. For example, the clipping threshold distance may be a position on the OCT image sufficiently far from an edge of the OCT image such that the quality of the OCT image is not distorted or of reduced quality.

According to a further example aspect there is provided a system for detecting clipping of retinal image data in an optical coherence tomography, OCT, image of a patient's retina, the system comprising: an input configured to receive an OCT image comprising retinal image data; a boundary detection module configured to detect a boundary of the retinal image data in the OCT image and further configured to calculate a distance between the boundary and an edge of the OCT image; a clipping detection module configured to determine if clipping of the retinal image data in the OCT image has occurred by comparing the calculated distance between the boundary and the edge of the OCT image with a clipping threshold distance; and an output configured to output a clipping notification indicative of a level of clipping of the retinal image data in the OCT image; wherein the clipping detection module is configured to determine that clipping of the retinal image data has occurred when the calculated distance between the boundary and the edge of the OCT image is equal to, or less than, the clipping threshold distance.

According to a further example aspect herein there is provided a system for detecting clipping of tissue image data in an optical coherence tomography, OCT, image of tissue, the system comprising: an input configured to receive an OCT image comprising tissue image data; a boundary detection module configured to detect a boundary of the tissue image data in the OCT image and further configured to calculate a distance between the boundary and an edge of the OCT image; a clipping detection module configured to determine if clipping of the tissue image data in the OCT image has occurred by comparing the calculated distance between the boundary and the edge of the OCT image with a clipping threshold distance; and an output configured to output a clipping notification indicative of a level of clipping of the tissue image data in the OCT image; wherein the clipping detection module is configured to determine that clipping of the tissue image data has occurred when the calculated distance between the boundary and the edge of the OCT image is equal to, or less than, the clipping threshold distance.

According to a yet further example aspect there is provided an optical coherence tomography system comprising the clipping detection system of any one of the aforementioned aspects and/or embodiments.

Within the scope of this application it is expressly intended that the various aspects, embodiments, examples and alternatives set out in the preceding paragraphs, and/or in the following description and drawings, and in particular the individual features thereof, may be taken independently or in any combination.

BRIEF DESCRIPTION OF THE DRAWINGS

Example embodiments will now be explained in detail, by way of non-limiting example only, with reference to the accompanying figures described below. Like reference numerals appearing in different ones of the figures can denote identical or functionally similar elements, unless indicated otherwise.

DETAILED DESCRIPTION

In general terms example embodiments herein relate to a method of detecting clipping of tissue image data in an optical coherence tomography, OCT, B-scan. The method comprises performing an OCT scan of body tissue, to acquire an OCT image of the tissue comprising tissue image data. The OCT image can be an OCT B-scan comprising tissue image data indicative of the imaged tissue. The position of a first boundary of the tissue image data, for example a top boundary, is detected in the acquired OCT image. The first boundary is indicative of a peripheral edge of the tissue image data in the OCT image. A distance between the first boundary and an edge of the OCT image is calculated. For example, a distance between the first boundary and an upper edge of the OCT B-scan may be calculated. The method further comprises determining if clipping of the tissue image data has occurred by comparing the calculated distance between the first boundary and the edge of the OCT image with a clipping threshold distance. Clipping of the tissue image data is determined to have occurred when the distance between the boundary and the edge of the OCT image is equal to or less than the clipping threshold distance.

A notification can be provided to a clinician of a level of clipping of an OCT image following an OCT scan being performed on a patient. For example, a clipping notification can be output to the clinician to provide an indication of a level of clipping of the tissue image data in the OCT image. If the tissue image data has been vertically clipped the clinician is notified such that the OCT scan can be repeated by the clinician to acquire an OCT image, such as a B-scan, that fully contains tissue image data indicative of the tissue to be imaged.

Figure 1:
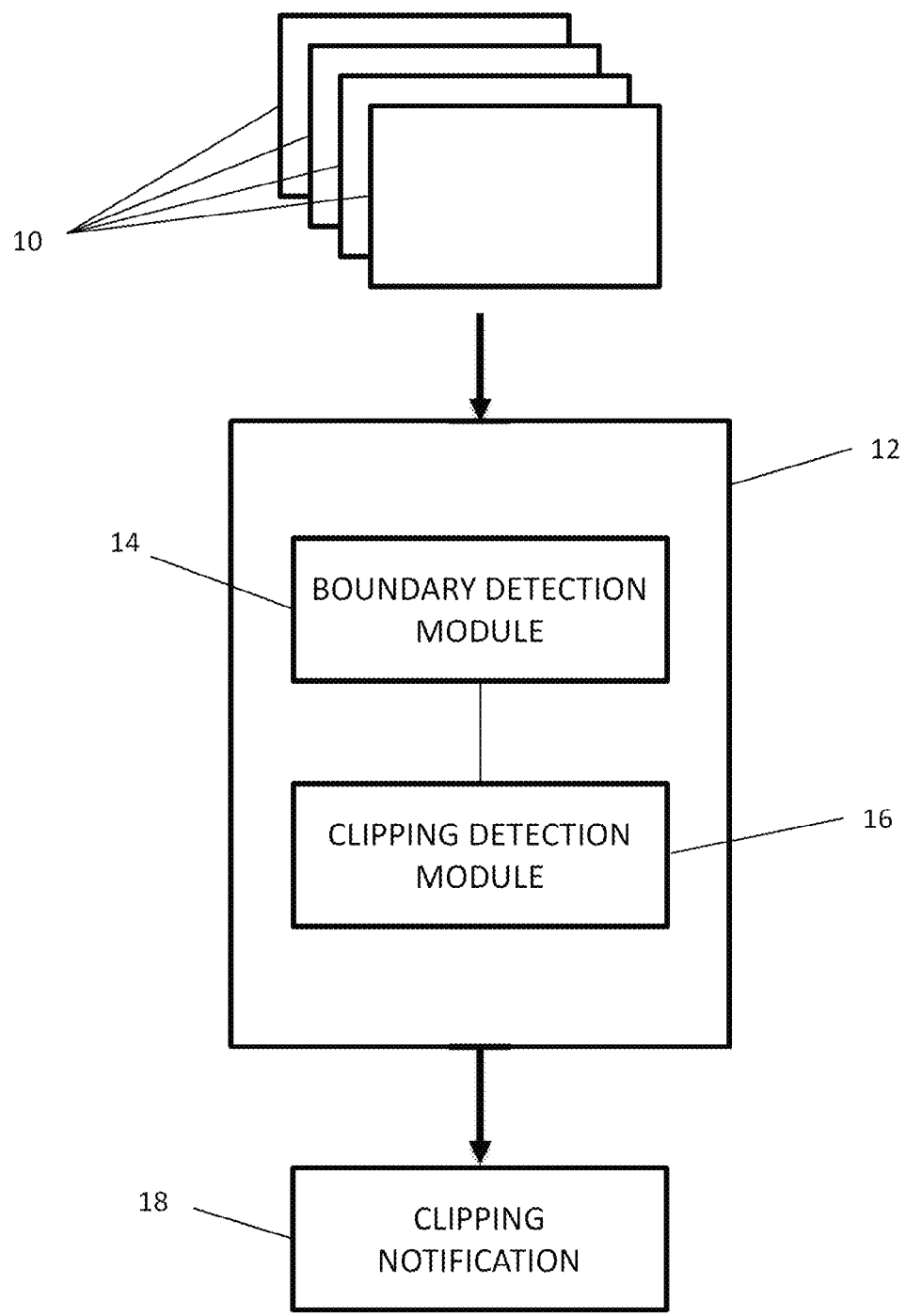
FIG. 1 is a schematic diagram of a system for detecting clipping of retinal imaging data in an OCT image according to an example embodiment herein.

To place example embodiments of the invention in a suitable context reference will firstly be made to FIG. 1 which shows a clipping detection system 12 for detecting clipping of retinal image content in an optical coherence tomography, OCT, image of a patient's eye. Example embodiments herein have been described in the context of detecting clipping of retinal image content in an OCT image. However, the skilled reader will appreciate that the clipping detection system 12 and associated methods can be used more generally to detect clipping of tissue image data in an OCT image wherein the tissue image data is image data indicative of an imaging target within the patient's tissue.

The clipping detection system 12 is configured to receive one or more OCT images 10, for example a stack of B-scans, comprising retinal image content or retinal image data 35 indicative of a patient's retina that has been acquired by an OCT imaging system (not shown). The retinal image content may be considered to be tissue image data relating to a patient's retina. The retinal image content may extend along a depth of the B-scan such that planes of varying depth of the retinal image content are captured in each A-scan to form the OCT image 10 or B-scan of the retinal image content. The system 12 is configured to detect clipping of the retinal image content in the OCT image 10 and to output a clipping notification 18 indicative of a level of clipping in the OCT image 10.

As shown in FIG. 1, the clipping detection system 12 comprises a boundary detection module 14 and a clipping detection module 16 communicatively coupled to each other. The boundary detection module 14 is configured to receive one or more OCT images 10 comprising retinal image data 35. Upon receipt of the OCT image 10 the boundary detection module 15 is configured to detect an upper and lower boundary of the retinal image data 35 indicative of an upper and lower boundary of the patient's retina in the OCT image 10. The upper and lower boundaries may be upper and lower peripheral edges of the retinal image data 35 in the OCT image 10 or B-scan. The boundary detection module 14 is configured to identify the upper and lower peripheral edges of the retinal image content in the OCT image 10 such that the clipping detection system 12 may determine if clipping of the retinal image data has occurred when acquiring the OCT image 10.

The clipping detection system 12 further comprises a clipping detection module 16 communicatively coupled to the boundary detection module 14. The clipping detection module 16 is configured to receive the OCT image 10 from the boundary detection module 14 wherein the position of the upper and lower boundaries of the retinal image data in the OCT image 10 have been identified by the boundary detection module 14. Identifying the position of the upper and lower boundaries of the retinal image data may comprise identifying the positional coordinates of points along the path of each boundary within the OCT image 10. For example, the boundary detection module 14 may employ image processing techniques to identify the location of the boundaries in the OCT image 10.

Upon receipt of the OCT image 10 from the boundary detection module 14 the clipping detection module 16 is configured to calculate a distance from the upper boundary of the retinal image data and an upper edge of the OCT image 10. Similarly, the boundary detection module 14 is further configured to calculate a distance from the lower boundary of the retinal image data and a lower edge of the OCT image 10. The clipping detection module is configured to identify regions where clipping of the retinal image data in the OCT image 10 has occurred. Clipping of the retinal image data 35 is determined by comparing the calculated distance between the upper and lower boundaries of the retinal image data and the respective upper and lower edges of the OCT image 10 with a clipping threshold distance. Locations within the OCT image 10 where the calculated distance between the upper and lower boundaries and the edge of the OCT image 10 is equal to or less than a clipping threshold distance are marked as being clipped by the clipping detection module 16. For example, the clipping detection module 16 may add a flag at each point in the OCT image 10 where the clipping detection module 16 determines that clipping of the retinal image data 35 has occurred.

Figure 2:
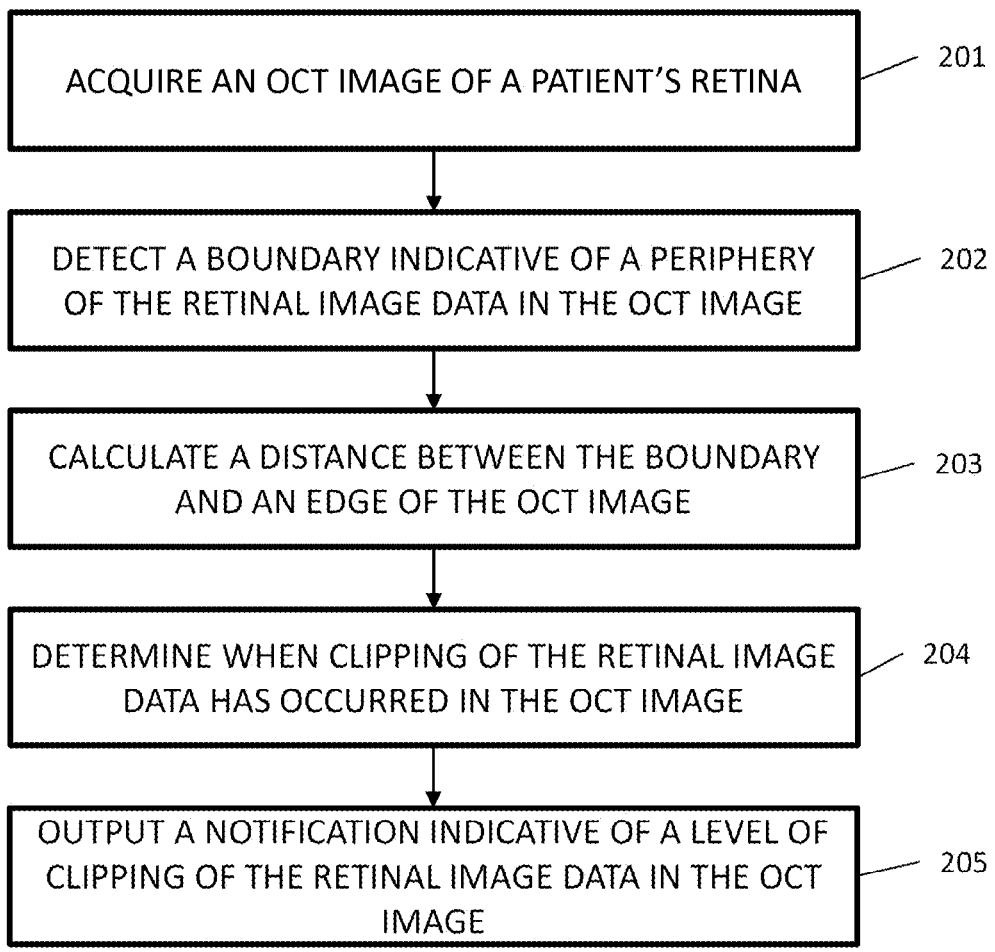
FIG. 2 is a flow diagram outlining a method of detecting clipping of retinal image data in an OCT image.

Turning now to FIG. 2 there is shown a flow diagram outlining a method of detecting clipping of retinal image data in an optical coherence tomography, OCT, image 10. In Step 201 an OCT image 10, such as a stack of B-scans, comprising retinal image data 35 indicative of a patient's retina is acquired. The OCT image 10 can be obtained by an OCT imaging system. The retinal image data 35 is at least partially contained within the OCT image 10 (see, for example, FIG. 3).

In Step 202 a boundary indicative of a periphery of the retinal image data 35 is detected in the OCT image 10. Detecting a boundary indicative of a periphery of the retinal image data 35 may comprise detecting the position of the retinal image data 35 within the OCT image 10. The retinal image data 35 may extend across a width of the OCT image 10. The boundary may be an upper boundary or a lower boundary of the retinal image data 35 in the OCT image 10. Next, in Step 203 a distance between the boundary of the retinal image data 35 and an edge of the OCT image 30 is calculated. For example, if the boundary of the retinal image data 35 is an upper boundary a distance between the boundary and an upper edge of the OCT image 10 may be calculated. Furthermore, if the boundary of the retinal image data 35 is a lower boundary a distance between the boundary and a lower edge of the OCT image 10 may be calculated.

In Step 204 the method comprises determining if clipping of the retinal image data 35 has occurred in the OCT image 10. Determining when clipping of the retinal image data 35 has occurred comprises comparing the calculated distance between the boundary and an edge of the OCT image 10 with a clipping threshold distance. Clipping of the retinal image data 35 is deemed to have occurred when the calculated distance is equal to or less than the clipping threshold distance. The distance between the boundary and the edge of the OCT image 10 may be calculated at points along the length of the boundary. The distance at each point and the edge of the OCT image 10 may be compared with the clipping threshold distance to determine locations or regions of clipping of the retinal image data 35.

The clipping threshold distance may be zero in some instances meaning that clipping is deemed to have occurred when the boundary of the retinal image data 35 contacts the edge of the OCT image 10. Alternatively, the clipping threshold distance may be an absolute value in terms of pixels. For example, clipping may be deemed to have occurred when the boundary of the retinal image data 35 is within 100 pixels of an edge of the OCT image 10. In an example embodiment herein, the clipping threshold distance can be a relative distance calculated in dependence on the dimensions of the OCT image 10. For example, a clipping threshold parameter with a value between 0 and 1 may be set by a user of the system 12 to calculate the clipping threshold distance. In this instance, clipping may be deemed to have occurred if the distance between the boundary and the edge of the OCT image data is equal to or less than the clipping threshold distance defined by the clipping threshold parameter multiplied by the height of the OCT image 10. The clipping threshold parameter may have a value of, for example, 0.05 in which case clipping is deemed to have occurred if the boundary is located within a distance equal to or less than 5% of the height of the OCT image 10 away from the edge of the OCT image 10.

Finally, in Step 205 a parameter indicative of a level of clipping in the OCT image 10 is output. The parameter may be a clipping notification 18. In an example embodiment herein, the method can comprise adding a clipping label to the OCT image 10 at a location(s) where clipping of the retinal image data 35 in the OCT image 10 is deemed to have occurred. The clipping notification 18 output may combine the number of clipping labels into a single clipping parameter indicative of a level of clipping. For example, the clipping parameter may be a clipping score used to grade the level of clipping in the retinal image data 35. The clipping score is an example of a clipping notification 18 indicative of a level of clipping of the retinal image data 35 in the OCT image 10.

Figure 3:
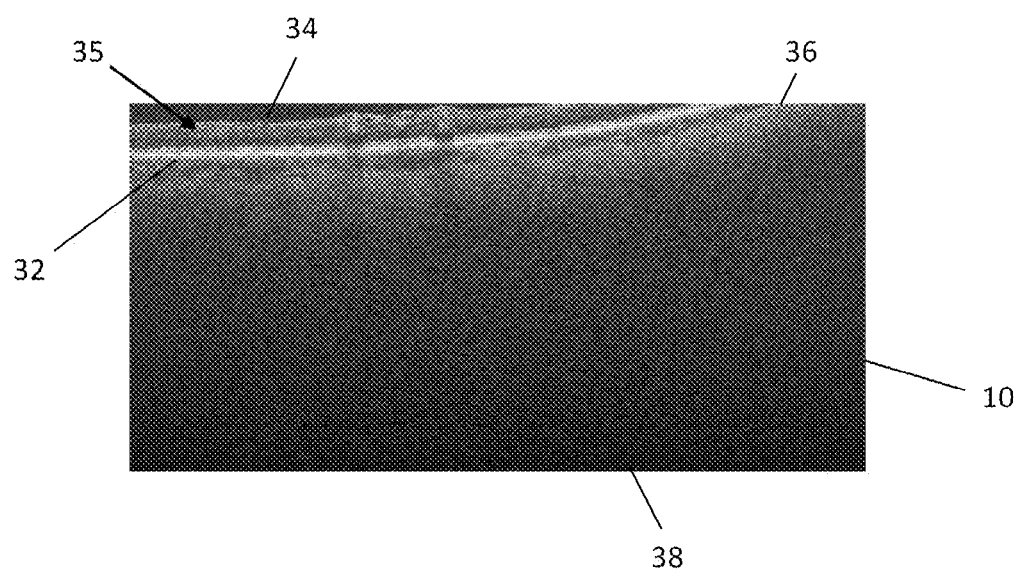
FIG. 3 is an example OCT image comprising retinal image data.

Turning now to FIG. 3 there is shown an example OCT image 10. The OCT image 10 in FIG. 3 is an example OCT image 10 of a patient's retina acquired by an OCT imaging system. The OCT image 10 comprises retinal image data 35 indicative of a patient's retina. As shown in FIG. 3 the retinal image data 35 has been vertically clipped. The retinal image data 35 is partially captured in the OCT image 10 between an upper OCT image edge 36 and a lower OCT image edge 38. The retinal image data 35 comprises a lower boundary 32 and an upper boundary 34 extending generally laterally across the OCT image 10.

As shown in FIG. 3 the upper boundary 34 of the retinal image data 35 is vertically clipped by the upper OCT image edge 36. The upper boundary 34 of the retinal image data 35 is generally arcuate such that it starts within the OCT image 10 on a left-hand side of the OCT image 10 before following an upward arcuate path laterally across the OCT image 10 such that the upper boundary 34 intersects the upper OCT image edge 36. As the upper boundary 34 extends upwardly towards the upper OCT image edge 36 clipping of the retinal image data 35 is determined to have occurred at the point where the upper boundary 34 is at a distance equal to or less than a clipping threshold distance away from the upper OCT image edge 36.

The tissue image data shown in FIG. 3 is an example where the tissue image data is retinal image data 35. However, in other embodiments the tissue image data may be representative of a different type of tissue. As shown in FIG. 3, the retinal image data 35 indicative of the patient's retina is positioned at an upper portion of the OCT image 10 which has resulted in a portion of the retinal image data 35 being vertically clipped by the upper OCT image edge 36. As a result, a portion of the patient's retina is cropped from the OCT image 10 such that it is not visible to a clinician. Clipping of the tissue image data in an OCT image 10 acquired by an OCT scanning system is often caused by the patient being aligned incorrectly relative to the OCT scanning system. If clipping is determined to have occurred, the clinician is notified by the clipping parameter 18 and the OCT scan can be repeated by the clinician. The clinician can realign the patient such that the tissue image data can be imaged without clipping of the tissue image data in the resultant OCT image 10.

Figure 4:
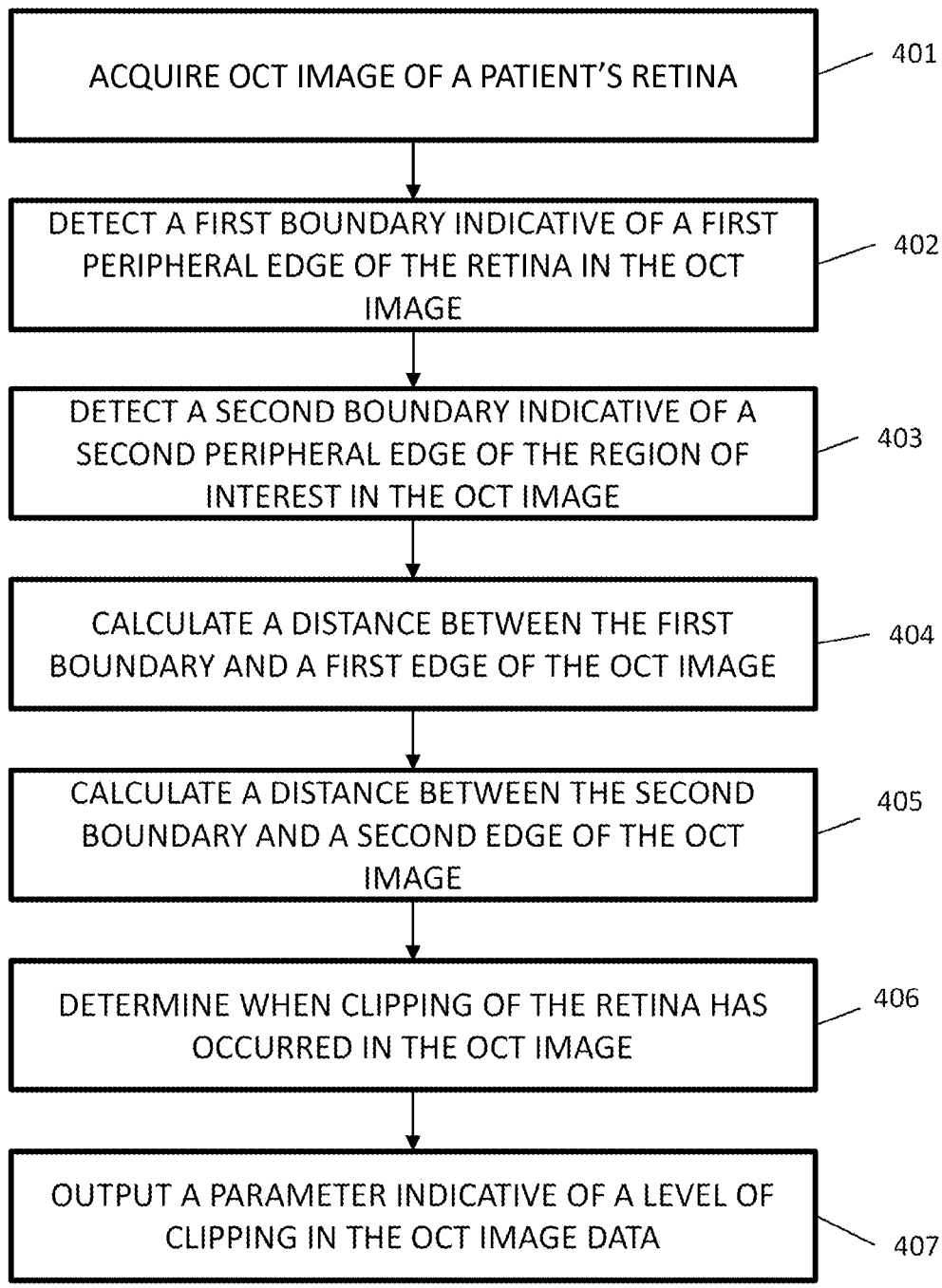
FIG. 4 is a flow diagram outlining a method of detecting clipping of retinal image data in an OCT image.

FIG. 4 shows a method of detecting clipping of tissue image data, and in particular clipping of retinal image data 35 indicative of a patient's retina, in an OCT image 10. In Step 401 an OCT image 10 of the patient's retina is acquired. The OCT image 10 may be one or more B-scans comprising retinal image data 35 of the patient's retina.

In Step 402 the location of a first or upper boundary 34 indicative of an upper peripheral edge of the retina or retinal image data 35 is detected in the OCT image 10 acquired in Step 401. In Step 403 the location of a second or lower boundary 32 indicative of a lower peripheral edge of the retina or retinal image data 35 is detected in the OCT image 10 acquired in Step 401. Detecting the location of the lower and upper boundaries 32, 34 may be performed by the boundary detection module 14 using image processing and/ or machine learning techniques. For example, edge detection after image filtering and enhancement may be used to detect the location of the lower and upper boundaries 32, 34 in the OCT image 10. Furthermore, machine learning techniques such as semantic segmentation and/or pixel labelling may be used to identify the location of the lower and upper boundaries 32, 34 in the OCT image 10.

In Step 404 a distance between the upper boundary 34 and the upper OCT image edge 36 is calculated. Similarly, in Step 405 a distance between the lower boundary 32 and the lower OCT image edge 38 is calculated. The distance may be an absolute distance, a distance relative to the dimensions of the OCT image 10 or a number of pixels in the OCT image 10.

In Step 406 locations in the OCT image 10 where the retinal image data 35 has been vertically clipped is determined. Determining if clipping of the retinal image data 35 has occurred comprises comparing the calculated distance between the upper and/or lower boundary 34, 32 with a clipping threshold distance. When the distance between the boundary 32, 34 and a respective edge of the OCT image 36, 38 is equal to or less than the clipping threshold distance then clipping of the retinal image data 35 is determined to have occurred. Step 406 may be repeated for points along the length of each of the lower and upper boundaries 32, 34 and a clipping marker may be added at each point where clipping of the retinal image data 35 is deemed to have occurred. The clipping marker may be a flag or the like indicative of clipping of the retinal image data 35 having taken place at a given location.

The clipping threshold distance may be specified by a user of the OCT imaging system prior to acquiring OCT images of the retina. For example, a user can specify a clipping threshold distance such that if the upper or lower boundary 34, 32 of the retinal image data 35 is equal to or less than the clipping threshold distance from the upper or lower edge 36, 38 of the OCT image 10 then clipping of the retinal image data 35 is deemed to have occurred. In an example embodiment herein, the clipping threshold distance can be a distance from an edge of the OCT image 10 where the quality of the image data within the OCT image 10 starts to degrade.

Alternatively, in another example embodiment herein, the clipping threshold distance may be defined relative to the size of the OCT image 30 or B-scan. For example, the clipping threshold can be a parameter or value indicative of a percentage of a height of the OCT image 10. For example, the clipping threshold parameter may be equal to 0.05 and clipping may be deemed to have occurred if the upper or lower boundary 34, 32 of the retinal image data 35 is a distance equal to or less than 0.05 times the height of the OCT image 10 from the upper or lower edge 36, 38.

The clipping threshold distance allows clipping of the retinal image data 35 to be determined even in instances where the retinal image data 35 is fully captured within the OCT image 10. For example, if the retinal image data 35 is captured within the OCT image 10 in a peripheral region where the quality of the OCT image 10 has started to degrade then it may be deemed that the retinal image data 35 has been clipped. In some embodiments the clipping threshold distance can be equal to zero such that clipping is deemed to have occurred when the lower or upper boundary 34,32 of the retinal image data 35 intersects a respective peripheral edge of the OCT image 10. The clipping threshold distance can be set in dependence on a level of degradation of image quality in the peripheral regions of the OCT image 10.

In Step 407 a parameter indicative of a level of clipping of the retinal image data 35 in the OCT image 10 is output. The parameter can be the clipping notification 18 indicative of a level of clipping of the retinal image data 35. The method may comprise adding a clipping label at a location where clipping of the retinal image data 35 in the OCT image 10 is deemed to have occurred. The parameter output may combine the number of clipping labels into a single parameter indicative of a level of clipping. For example, the clipping notification 18 can be a clipping score used to grade the level of clipping of the retinal image data 35 in the OCT image 10.

In an example embodiment herein, the clipping notification 18 or parameter indicative of the level of clipping in the OCT image 10 can be generated and output upon completion of the OCT scan. As such, the clipping notification 18 can provide real-time or substantially real-time feedback to a clinician relating to a level of clipping in the OCT images acquired by the scan. For example, the clipping notification 18 may be output within one to ten minutes after completion of the OCT scan. If the clipping notification 18 output indicates a high level of clipping, then the clinician can repeat the OCT scan to ensure that high quality OCT images of the patient's retina may be acquired by the OCT scan.

The clipping notification 18 indicative of a level of clipping can take various forms suitable to convey a severity of vertical clipping in the OCT image 10 to a clinician. For example, the clipping notification 18 may be a numerical quality score. The numerical quality score may indicate the number of B-scans affected by vertical clipping in the OCT image 10. Furthermore, the numerical quality score may include information about whether the clipping occurred on the top and/or the bottom of each of the OCT images 10 that were affected by vertical clipping. For example, two clipping notifications 18 may be output wherein each clipping notification is indicative of a level of clipping of a respective edge of the OCT image 10.

Alternatively, the clipping notification 18 can be an en-face image of the patient's retina. The en-face image may be marked such that regions affected by vertical clipping are visually highlighted such that a clinician may readily identify areas that have been vertically clipped. The clipping notification 18 may be a clipping region overlaid on the en-face image of the patient's retina. The clipping notification 18 may also take the form of a Boolean array of size 1×n wherein, n, is the number of input B-scans or OCT images 10. The Boolean array may include information indicating which of the B-scans contain retinal image data 35 that has been clipped and also whether the top and/or bottom of the retinal image data 35 in each B-scan is clipped.

Figure 5:
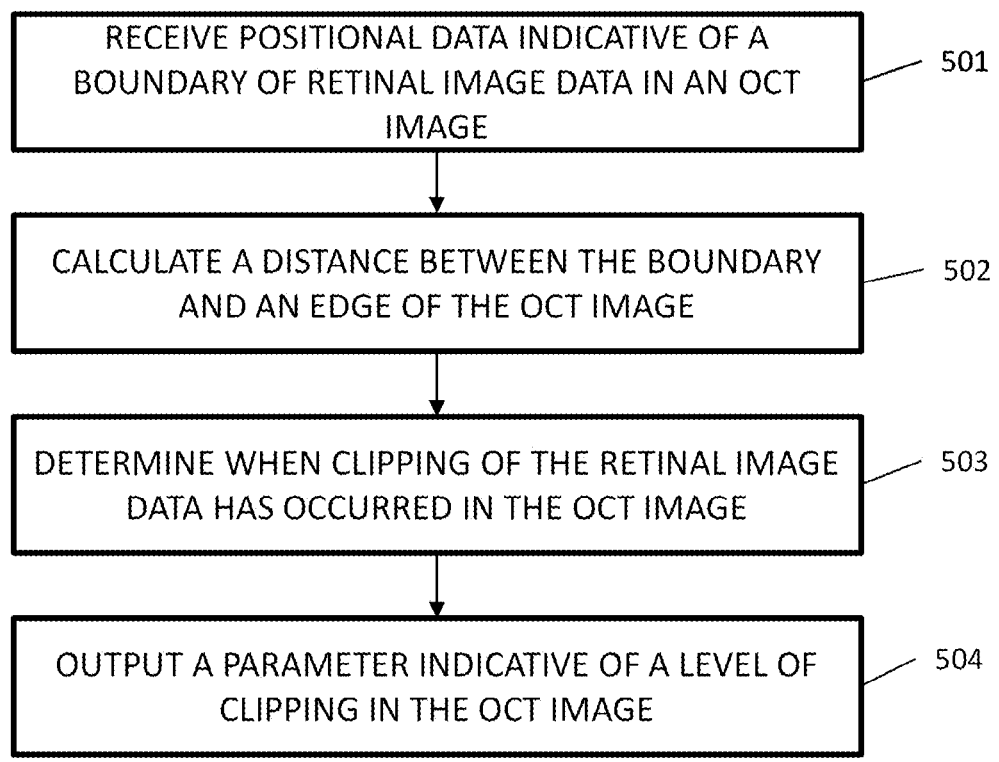
FIG. 5 is a flow diagram outlining a method of compensating for retinal movements when detecting clipping of retinal image data in an OCT image.

Turning now to FIG. 5 there is shown a flow diagram outlining a method of detecting vertical clipping of retinal image data 35 in an OCT image 10. In Step 501 positional data indicative of a position of the lower and/or upper boundary 34, 32 of the retinal image data 35 is received. The positional data can be one or more stacks of arrays comprising coordinates indicative of the position of the upper and/or lower boundary 34, 32 of the retinal image data 35 in the OCT image 10. For example, the input may be a first stack of arrays each of a size 1×w and a second stack of arrays each of a size 1×w, wherein w is the width of the OCT image 10. The first stack of arrays may comprise positional data indicative of a position of the upper boundary 34 of the retinal image data 35 and the second stack of arrays may comprise positional data indicative of a position of the lower boundary 32 of the retinal image data 35.

In Step 502 a distance between the upper and/or lower boundary 34, 32 of the retinal image data 35 and the upper and/or lower edge 36, 38 of the OCT image 10 is calculated. Calculating the distance between the upper and/or lower boundary 34, 32 and the respective upper and/or lower edge 36, 38 of the OCT image 10 may comprise comparing the coordinates of the upper and/or lower boundary 34, 32 at discrete points over the width, w, of the OCT image 10 with a position of the respective upper and/or lower edge 36, 38 of the OCT image 10.

In Step 503 the method comprises determining when clipping of the retinal image data 35 has occurred in the OCT image 10. Clipping of the retinal image data 35 is deemed to have occurred when the distance between the boundary 32, 34 and the edge of the OCT image 10 is equal to or less than the distance defined by the clipping threshold distance.

In Step 504 a clipping notification 18 indicative of a level of clipping in the OCT image 10 is output. The clipping notification 18 can be a flag or marker at each discrete point where vertical clipping of the retinal image data 35 is determined to have occurred within the OCT image 10. Furthermore, the clipping notification 18 may be a quality score or clipping level indicator configured to provide an indication of a level of clipping in the OCT image 10 to a clinician.

Figure 6:
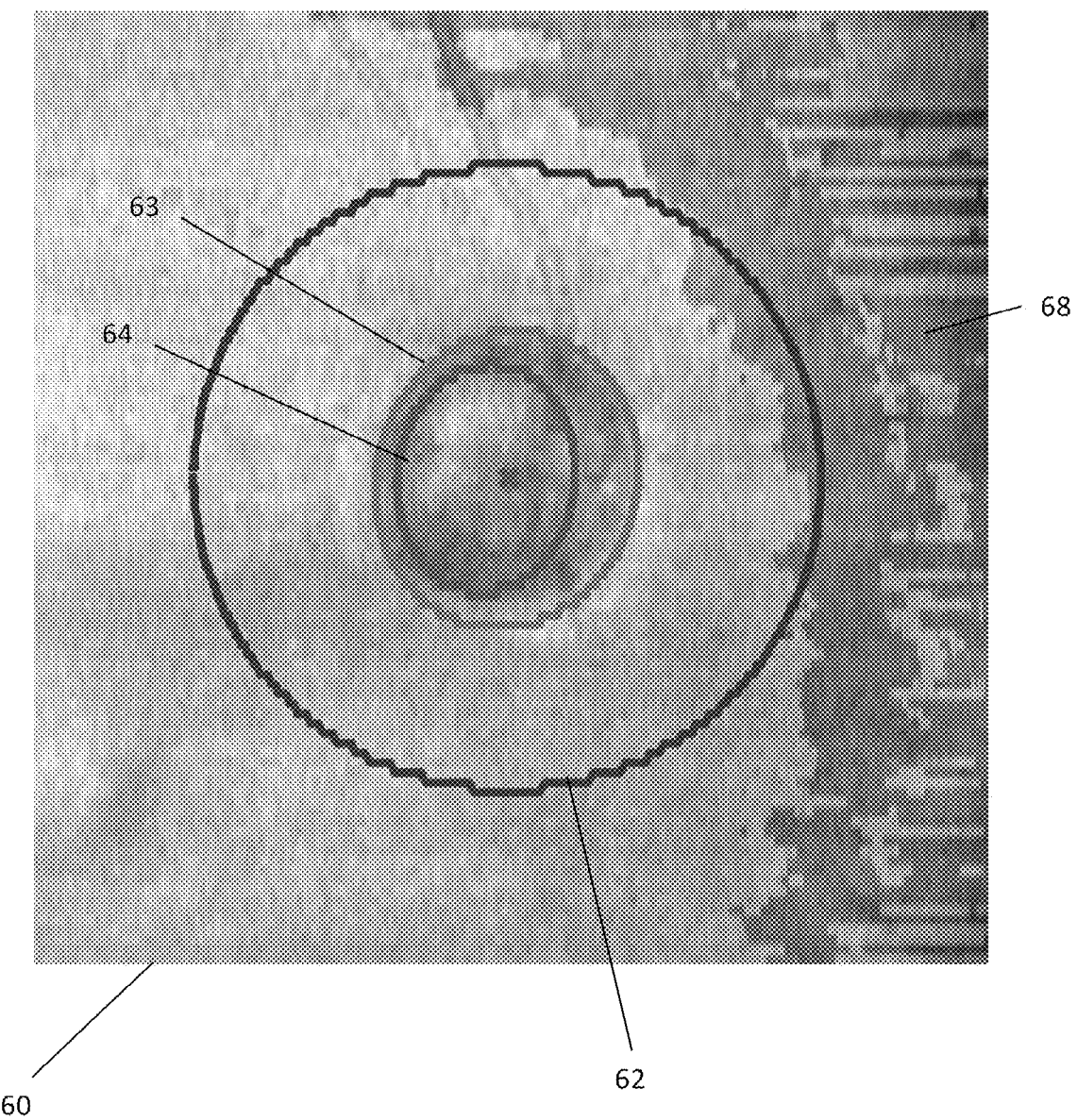
FIG. 6 is an example en-face image of a patient's retina comprising a region of interest and a masked region.

Turning now to FIG. 6 there is shown an en-face image 60 of a patient's retina. The en-face image 60 of the patient's retina includes a clipped region 68 overlaid on the en-face image 60 representative of regions of the retina that have been vertically clipped during OCT image acquisition. The clipped region 68 provides a visual indication to a clinician of the regions of the patient's retina that have been vertically clipped during image acquisition. The clipped region 68 can be a clipping notification 18 output by the clipping detection system 12.

The clinician may specify a masked region 62 surrounding the region of interest 63 on the en-face image 60. The region of interest 63 may be an area comprising an anatomical feature 64 to be imaged by an OCT imaging system. If clipping of retinal image data 35 in the OCT image 10 of the patient's retina occurs outside the masked region 62 the system 12 may determine that although clipping of retinal image data 35 has occurred it does not adversely affect the image of the region of interest 63 within the masked region 62 and thus the clipping notification 18 output by the system 12 may indicate to a clinician that whilst the OCT image 10 has been clipped, clipping of the region of interest 63 has not occurred. As shown in FIG. 6 the masked region 62 is larger than the region of interest 63 such that the region of interest 63 is contained within the masked region 62.

As shown in the example en-face image 60 of FIG. 6 the clipped region 68 partially extends into the masked region 62 but does not contact the region of interest 63. In this example as the masked region 62 has been clipped the region of interest 63 is also deemed to have been vertically clipped and as such a clipping notification 18 may be output to the clinician to convey that the OCT scan should be repeated to avoid vertical clipping of the region of interest 63. The masked region 62 allows a clinician to discard vertical clipping detected outside the masked region 62 as clipping outside the masked region 62 does not adversely affect the resultant retinal image data 35 of the region of interest 63 containing the anatomical feature 64 to be imaged. This can make the OCT imaging process quicker and more efficient by reducing false positives indicating clipping of the retinal image data 35 being output by the system 12.

In an example embodiment herein, movement data indicative of a movement of the patient's eye during acquisition of the OCT image(s) 10 is input to the clipping detection system 12. The movement data may be movement indicative of retinal movement of a patient's eye resulting in movement of the retinal image data 35 within the OCT image 10. The method of determining if clipping of retinal image data 35 has occurred may comprise compensating for movements of the patient's eye, and thus retinal image data 35, prior to determining if clipping of the retinal image data 35 or masked region 62 has occurred. Compensating for movement of the retinal image data 35 may comprise receiving the movement data and subsequently moving the retinal image data 35 within each B-scan or OCT image 10 upwards or downwards by a number of pixels specified in the movement data such that the retinal image data within the OCT image 10 or stack of B-scans is aligned along the depth axis of the B-scans. Moving the retinal imaged data 35 upwards or downwards may comprise moving the lower and/or upper boundary 32, 34 in an upward or downward direction prior to calculating a distance between the lower and/or upper boundary 32, 34 and an edge of the OCT image 36, 38. The movement data may be acquired by retinal tracking or the like during OCT image acquisition.

Figure 7:
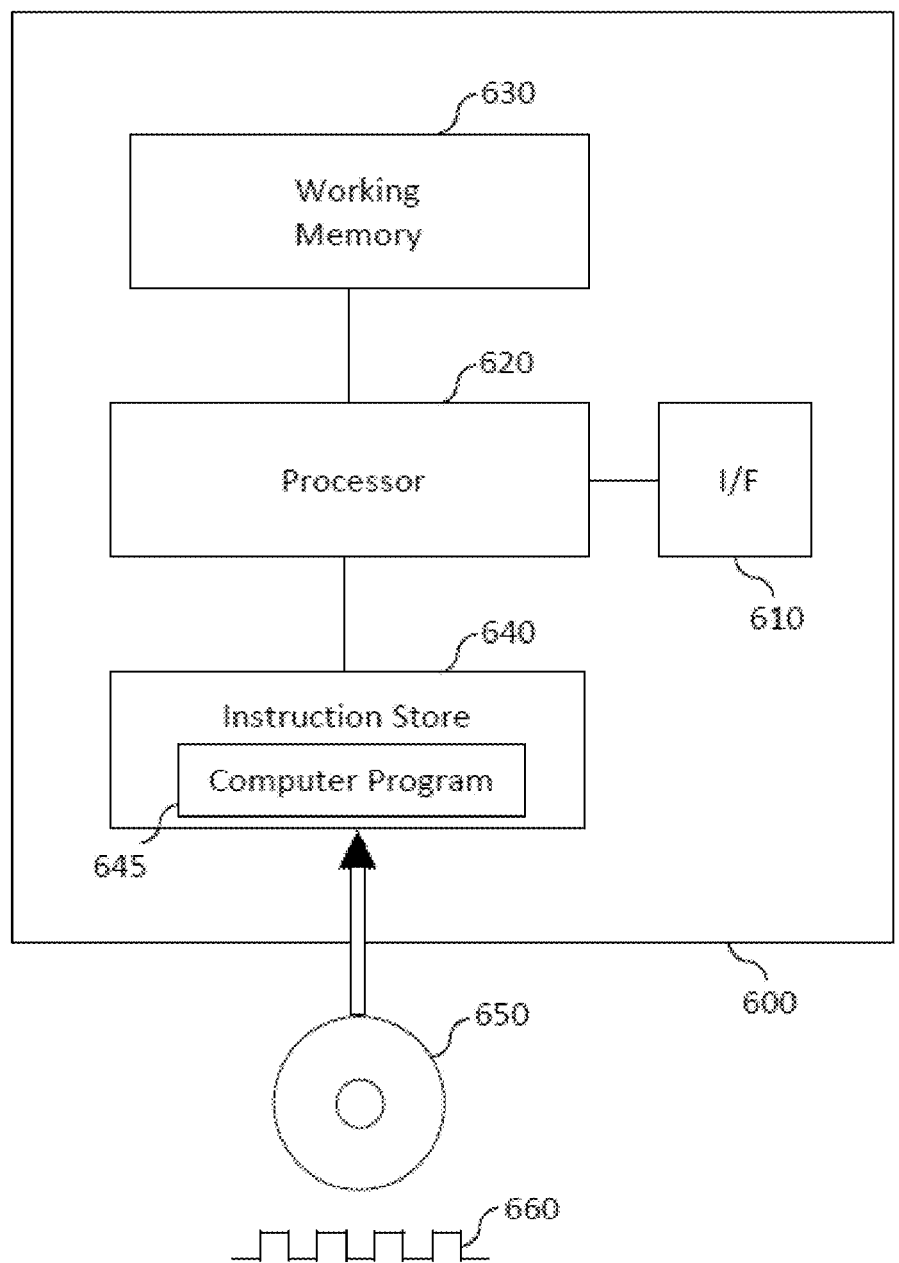
FIG. 7 is an example hardware implementation of an apparatus that can operate as a system for detecting vertical clipping according to an example embodiment herein.

FIG. 7 is a schematic illustration of a programmable signal processing hardware 600, configured to detect vertical clipping of retinal image data 35 in an OCT image 10. The programmable signal processing hardware 600 can perform the functionalities of the clipping detection system 12, and, in one example embodiment herein, at least part of the hardware 600 is included in the clipping detection system 12. The programmable signal processing apparatus 600 comprises a communication interface (I/F) 610, for receiving an OCT image 10 from an OCT imaging system (not shown), and for outputting a clipping notification 18. In one example embodiment herein, the communication interface (I/F) 610 can input/output any information obtained as part of the methods described herein.

The signal processing apparatus 600 further comprises a processor (e.g. a Central Processing Unit, CPU, and/or a Graphics Processing Unit, GPU) 620, a working memory 630 (e.g. a random access memory) and an instruction store 640 storing a computer program 645 comprising computer-readable instructions which, when executed by the processor 620, cause the processor 620 to perform various functions including those of the clipping detection system 12 including the functions of the boundary detection module 14, and/or the functions of the clipping detection module 16 described herein. In one example embodiment herein, only the processor 620 is included in the clipping detection system 12, although in other examples one or more additional components of the hardware 600 also are included in the clipping detection system 12 as well.

The working memory 630 stores information used by the processor 620 during execution of the computer program 645. The instruction store 640 comprises, for example, a ROM (e.g. in the form of an electrically erasable programmable read-only memory (EEPROM) or flash memory) which is pre-loaded with the computer-readable instructions. Alternatively, the instruction store 640 comprises a RAM or similar type of memory, and the computer-readable instructions of the computer program 645 can be input thereto from a computer program product, such as a non-transitory, computer-readable storage medium 650 in the form of a CD-ROM, DVDROM, etc. or a computer-readable signal 660 carrying the computer-readable instructions. In any case, the computer program 645, when executed by the processor 620, causes the processor 620 to perform the methods described herein, including by example and without limitation, a method of detecting clipping of retinal image data 35 in an OCT image 10 as described hereinabove. In one example embodiment herein, the clipping detection system 12 of the example embodiments described above comprises the computer processor 620 and memory 640 storing the computer-readable instructions which, when executed by the computer processor 620, cause the computer processor 620 to perform the methods described herein, including by example and without limitation, a method of detecting clipping of retinal image data 35 in an OCT image 10 as described herein.

In the foregoing description, example aspects are described with reference to several example embodiments. Accordingly, the specification should be regarded as illustrative, rather than restrictive. Similarly, the figures illustrated in the drawings, which highlight the functionality and advantages of the example embodiments, are presented for example purposes only. The architecture of the example embodiments is sufficiently flexible and configurable, such that it may be utilised in ways other than those shown in the accompanying figures.

Software embodiments of the examples presented herein may be provided as, a computer program, or software, such as one or more programs having instructions or sequences of instructions, included or stored in an article of manufacture such as a machine-accessible or machine-readable medium, an instruction store, or computer-readable storage device, each of which can be non-transitory, in one example embodiment. The program or instructions on the non-transitory machine-accessible medium, machine-readable medium, instruction store, or computer-readable storage device, may be used to program a computer system or other electronic device. The machine- or computer-readable medium, instruction store, and storage device may include, but are not limited to, floppy diskettes, optical disks, and magneto-optical disks or other types of media/machine-readable medium/instruction store/storage device suitable for storing or transmitting electronic instructions. The techniques described herein are not limited to any particular software configuration. They may find applicability in any computing or processing environment. The terms "computer-readable", "machine-accessible medium", "machine-readable medium", "instruction store", and "computer-readable storage device" used herein shall include any medium that is capable of storing, encoding, or transmitting instructions or a sequence of instructions for execution by the machine, computer, or computer processor and that causes the machine/computer/computer processor to perform any one of the methods described herein. Furthermore, it is common in the art to speak of software, in one form or another (e.g., program, procedure, process, application, module, unit, logic, and so on), as taking an action or causing a result. Such expressions are merely a shorthand way of stating that the execution of the software by a processing system causes the processor to perform an action to produce a result.

Some embodiments may also be implemented by the preparation of application-specific integrated circuits, field-programmable gate arrays, or by interconnecting an appropriate network of conventional component circuits.

Some embodiments include a computer program product. The computer program product may be a storage medium or media, instruction store(s), or storage device(s), having instructions stored thereon or therein which can be used to control, or cause, a computer or computer processor to perform any of the procedures of the example embodiments described herein. The storage medium/instruction store/storage device may include, by example and without limitation, an optical disc, a ROM, a RAM, an EPROM, an EEPROM, a DRAM, a VRAM, a flash memory, a flash card, a magnetic card, an optical card, nanosystems, a molecular memory integrated circuit, a RAID, remote data storage/archive/warehousing, and/or any other type of device suitable for storing instructions and/or data.

Stored on any one of the computer-readable medium or media, instruction store(s), or storage device(s), some implementations include software for controlling both the hardware of the system and for enabling the system or microprocessor to interact with a human user or other mechanism utilizing the results of the example embodiments described herein. Such software may include without limitation device drivers, operating systems, and user applications. Ultimately, such computer-readable media or storage device(s) further include software for performing example aspects of the invention, as described above.

Included in the programming and/or software of the system are software modules for implementing the procedures described herein. In some example embodiments herein, a module includes software, although in other example embodiments herein, a module includes hardware, or a combination of hardware and software.

While various example embodiments of the present invention have been described above, it should be understood that they have been presented by way of example, and not limitation. It will be apparent to persons skilled in the relevant art(s) that various changes in form and detail can be made therein. Thus, the present invention should not be limited by any of the above described example embodiments, but should be defined only in accordance with the following claims and their equivalents.

It is also to be understood that any procedures recited in the claims need not be performed in the order presented.

While this specification contains many specific embodiment details, these should not be construed as limitations on the scope of any inventions or of what may be claimed, but rather as descriptions of features specific to particular embodiments described herein. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

In certain circumstances, multitasking and parallel processing may be advantageous. Moreover, the separation of various components in the embodiments described above should not be understood as requiring such separation in all embodiments, and it should be understood that the described program components and systems can generally be integrated together in a single software product or packaged into multiple software products.

Having now described some illustrative embodiments and embodiments, it is apparent that the foregoing is illustrative and not limiting, having been presented by way of example. In particular, although many of the examples presented herein involve specific combinations of apparatus or software elements, those elements may be combined in other ways to accomplish the same objectives. Acts, elements and features discussed only in connection with one embodiment are not intended to be excluded from a similar role in other embodiments or embodiments.

The invention claimed is:

1. A method of detecting vertical clipping of retinal image data in an optical coherence tomography, OCT, image of a patient's retina, the method comprising:
    detecting a boundary of the retinal image data that is indicative of a boundary of the patient's retina in the OCT image;
    calculating a distance between the boundary and an edge of the OCT image;
    determining if vertical clipping of the retinal image data in the OCT image has occurred by comparing the calculated distance between the boundary and the edge of the OCT image with a clipping threshold distance, wherein clipping of the retinal image data is determined to have occurred when the calculated distance between the boundary and the edge of the OCT image is equal to, or less than, the clipping threshold distance; and
    outputting a clipping notification by overlaying a clipping region on an en-face image of the patient's retina, wherein the clipping region provides a visual indication of one or more areas of the retinal image data that have been vertically clipped.

2. A method as claimed in claim 1 comprising:
    detecting a second boundary of the retinal image data that is indicative of a second boundary of the patient's retina in the OCT image;
    calculating a distance between the second boundary and a second edge of the OCT image; and
    determining if clipping of the retinal image data has occurred by comparing the distance between the second boundary and the second edge of the OCT image with the clipping threshold distance;
    wherein clipping of the retinal image content is determined to have occurred when the distance between the second boundary and the second edge of the OCT image is equal to, or less than, the clipping threshold distance.

3. A method as claimed in claim 2, wherein the boundary is an upper boundary of the retinal image data that is indicative of an upper boundary of the patient's retina, and wherein the second boundary is a lower boundary of the retinal image data that is indicative of a lower boundary of the patient's retina.

4. A method as claimed in claim 3, wherein calculating the distance between the boundary and the edge of the OCT image comprises calculating a distance between the upper boundary and an upper edge of the OCT image; and calculating the distance between the second boundary and the second edge of the OCT image comprises calculating a distance between the lower boundary and a lower edge of the OCT image.

5. A method as claimed in claim 1, wherein the clipping notification is indicative of a level of clipping of the retinal image data in the OCT image.

6. A method as claimed in claim 5, wherein the OCT image comprises B-scans, and the clipping notification comprises one of:
    a numerical quality score indicating a number of B-scans affected by a vertical clipping in the OCT image; or
    a Boolean array of size 1×n, where n is the number of the B-scans, the Boolean array including information indicating which of the B-scans contain retinal image data that has been clipped.

7. A method as claimed in claim 5, wherein the method further comprises determining whether an instance of vertical clipping of the retinal image data has occurred outside a masked region surrounding a region of interest on the en-face image of the patient's retina and, in case the instance of vertical clipping of the retinal image data is determined to have occurred outside the masked region, omitting the instance of vertical clipping from the one or more areas of the visual indication.

8. A method as claimed in claim 7, wherein the region of interest comprises an anatomical feature on the patient's retina.

9. A method as claimed in claim 1, comprising receiving positional data indicative of a position of the patient's eye and moving the detected boundary of the retinal image data within the OCT image based on the received positional data.

10. A method as claimed in claim 1, further comprising acquiring the OCT image wherein the OCT image is one or more B-scans.

11. A method as claimed in claim 1, further comprising receiving an array of boundary data indicative of a position of the boundary in the OCT image.

12. A method as claimed in claim 1, wherein the clipping threshold distance is either equal to zero or is defined as a function of a dimension of the OCT image.

13. A non-transitory computer-readable storage medium comprising computer-readable instructions that, when executed by a processor, cause the processor to perform a method of detecting vertical clipping of retinal image data in an optical coherence tomography, OCT, image of a patient's retina, the method comprising:
    detecting a boundary of the retinal image data that is indicative of a boundary of the patient's retina in the OCT image;
    calculating a distance between the boundary and an edge of the OCT image;
    determining if vertical clipping of the retinal image data in the OCT image has occurred by comparing the calculated distance between the boundary and the edge of the OCT image with a clipping threshold distance, wherein clipping of the retinal image data is determined to have occurred when the calculated distance between the boundary and the edge of the OCT image is equal to, or less than, the clipping threshold distance; and
    outputting a clipping notification by:
    overlaying a clipping region on an en-face image of the patient's retina, wherein the clipping region provides a visual indication of one or more areas of the retinal image data that have been vertically clipped; or
    in case where vertical clipping of the retinal image data is determined to have occurred outside a masked region surrounding a region of interest on the en-face image, indicating that clipping of the region of interest has not occurred.

14. A system for detecting vertical clipping of retinal image data in an optical coherence tomography, OCT, image of a patient's retina, the system comprising:
    an input arranged to receive an OCT image comprising retinal image data;
    a boundary detection module arranged to detect a boundary of the retinal image data in the OCT image and further arranged to calculate a distance between the boundary and an edge of the OCT image;
    a clipping detection module arranged to determine if clipping of the retinal image data that is indicative of a boundary of the patient's retina in the OCT image has occurred by comparing the calculated distance between the boundary and the edge of the OCT image with a clipping threshold distance; and an output arranged to output a clipping notification indicative of a level of clipping of the retinal image data in the OCT image, wherein:

the clipping detection module is arranged to determine that clipping of the retinal image data has occurred when the calculated distance between the boundary and the edge of the OCT image is equal to, or less than, the clipping threshold distance, and the clipping notification comprises an en-face image of the patient's retina on which a clipping region is overlaid to provide a visual indication of one or more areas of the retinal image data that have been vertically clipped.

* * * * *